United States Patent [19]

Hozumi et al.

[11] 4,426,525

[45] Jan. 17, 1984

[54] CERTAIN PHOSPHORIC ACID ESTER DERIVATIVES OF 1,3-DIOXY PROPANE

[75] Inventors: Motoo Hozumi, Omiya; Susumu Tsushima, Suita; Yoshio Yoshioka, Nara, all of Japan

[73] Assignee: Takeda Chemical Industries, Ltd., Osaka, Japan

[21] Appl. No.: 311,876

[22] Filed: Oct. 15, 1981

[30] Foreign Application Priority Data

Oct. 22, 1980 [JP] Japan ................................ 55-148485

[51] Int. Cl.³ ........................... C07F 9/38; C07F 9/58; C07F 9/65
[52] U.S. Cl. ..................................... 546/22; 548/112; 260/945; 260/925; 424/263
[58] Field of Search .......................... 546/22; 548/112; 260/925, 945

[56] References Cited

U.S. PATENT DOCUMENTS 4,159,988  7/1979  Eibl et al. ..................... 260/340.9 R

FOREIGN PATENT DOCUMENTS 772648  2/1978  South Africa ..................... 260/945
772649  2/1978  South Africa ..................... 260/945

*Primary Examiner*—Alan L. Rotman
*Attorney, Agent, or Firm*—Wegner & Bretschneider

[57] ABSTRACT

Tridecyloxy- or tetradecyloxy-propane derivatives of the formula:

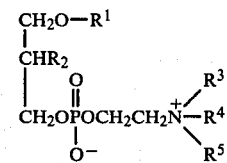

wherein $R^1$ is tridecyl or tetradecyl, $R^2$ is hydrogen or —OCH$_3$, and $R^3$, $R^4$ and $R^5$ independently represent hydrogen or $C_{1-3}$ alkyl, or

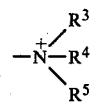

represents cyclic ammonio, and their salts, have inhibitory activity to multiplication of tumor cells and antimicrobial activity.

5 Claims, No Drawings

CERTAIN PHOSPHORIC ACID ESTER DERIVATIVES OF 1,3-DIOXY PROPANE

This invention relates to tridecyloxy- or tetradecyloxypropane derivatives which are of value as medicines and antimycotic agents.

More particularly, this invention relates to a pharmaceutical composition which comprises, as an active ingredient, an effective amount of a compound of the formula:

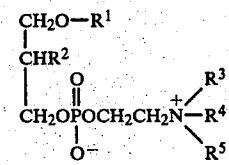

wherein
R$^1$ is tridecyl or tetradecyl,
R$^2$ is hydrogen or —OCH$_3$, and
R$^3$, R$^4$ and R$^5$ independently represent hydrogen or C$_{1-3}$ alkyl, or

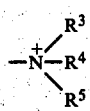

represents cyclic ammonio, or a pharmaceutically acceptable salt thereof, in association with a pharmaceutically acceptable carrier, and relates to novel tridecyloxy- or tetradecyloxy-propane derivatives which are compounds of formula (I) wherein all the symbols are as defined above, provided that when R$^1$ is tetradecyl and R$^2$ is hydrogen,

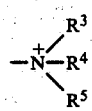

represents cyclic ammonio, and their pharmaceutically acceptable salts.

As examples of the C$_{1-3}$ alkyl group representable by R$^3$, R$^4$ and R$^5$ in the above formula (I), there may be mentioned methyl and ethyl. In case where at least one of R$^3$, R$^4$ and R$^5$ is hydrogen, for example, when R$^3$ is hydrogen, the compound (I) may also be shown by the following formula (Ia):

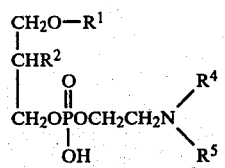

wherein all the symbols are as defined above.

Referring to the above formula (I), the cyclic ammonio group shown by

includes, among others, pyridinio oxazolio, thiazolio, pyridazinio, quinolinio or isoquinolinio, and these groups may have a substituent such as hydroxymethyl, hydroxyiminomethyl, amino(imino), trimethylammonio, carbamoyl, ureido, carboxyl, sulfo, methanesulfonyl, sulfamoyl, methyl or ethyl. The above-mentioned cyclic ammonio group includes such a case where optional two groups among R$^3$, R$^4$ and R$^5$ from a ring with the quaternary nitrogen atom and the remaining one group is methyl or ethyl, more concretely to state, they form N-methylmorpholinio or N-methylpiperidinio, for instance.

In Compound (I), when R$^2$ is methoxy, two types of stereoisomers, i.e. R-configuration and S-configuration are included, and each of them, a mixture of them and RS-isomer are all within the scope of this invention.

It should be understood that Compound (I) may also exist in the form of a pharmaceutically acceptable salt, for example, a salt having the formula:

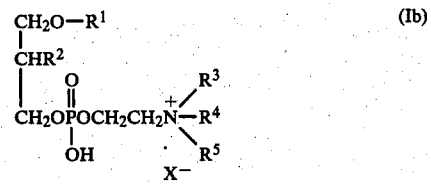

wherein X$^-$ is an anion (e.g. Cl$^-$ or Br$^-$), and all other symbols are as defined above, or a salt of the formula:

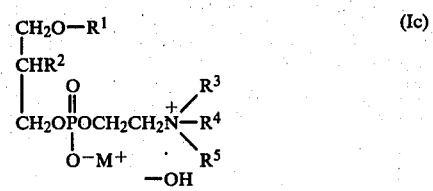

wherein M$^+$ is an alkali metal (e.g. Na, K) ion or an alkaline earth metal (e.g. Ca, Mg) ion, and all other symbols are as defined above.

Representative examples of Compound (I) to be used as the pharmaceutical composition of this invention are:
  3-tridecyloxy-2-methoxypropyl 2-trimethylammonioethyl phosphate,
  3-tetradecyloxy-2-methoxypropyl 2-trimethylammonioethyl phosphate,
  3-tridecyloxy-2-methoxypropyl 2-aminoethyl phosphate,
  3-tridecyloxypropyl 2-trimethylammonioethyl phosphate,
  3-tetradecyloxypropyl 2-trimethylammonioethyl phosphate,
  3-tetradecyloxypropyl 2-aminoethyl phosphate,
  3-tridecyloxy-2-methoxypropyl 2-pyridinioethyl phosphate,
  3-tridecyloxypropyl 2-thiazolioethyl phosphate, and
  3-tetradecyloxypropyl 2-(4-carbamoylpyridino)ethyl phosphate.

Compounds analogous to Compound (I) of this invention, namely those representable by the formula (I) wherein $R^1$ stands for octadecyl group, hexadecyl group, dodecyl group or decyl group, are known by the disclosures in, among others, Cancer Research, 38, pp. 339–344, 3894–3899 (1978), 39, pp. 4681–4686 (1979), Japanese Patent Unexamined Publication Nos. (Tokkai Sho) 52-134027 and 54-84530, but, in Annalen der Chemie 709, pp. 234–244 (1967) which is cited in these publications as a reference material for the synthesis, no disclosure relating to the afore-mentioned compounds themselves is found. Furthermore, no disclosure concerning the synthesis of Compound (I) is found in generally known literature references. When the synthesis of these compounds is intended, even men skilled in the art can hardly start for the work without preparatory professional study on the methods and conditions of the reaction and separation of the reaction product and further on the structural determination of the reaction product. To state further, Compound (I) wherein $R^1$ stands for tridecyl group, Compound (I) wherein $R^1$ stands for tetradecyl and $R^2$ stands for $-OCH_3$ and Compound (I) wherein $R^1$ stands for tetradecyl, $R^2$ stands for hydrogen and

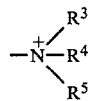

stands for cyclic ammonio are novel compounds which have never been disclosed in literature references. Circumstances being as above, the following are the first disclosure of the methods of preparing Compound (I).

Process A

Compound (I) can be produced by reacting a compound of the formula:

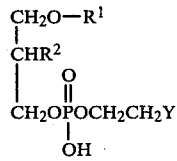

(II)

wherein $R^1$ and $R^2$ are as defined above and Y is hydrogen, with a compound of the formula:

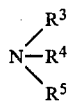

(III)

wherein all the symbols are as defined above or

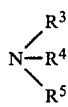

represents cyclic amine which corresponds to cyclic ammonio as defined above.

The compound (III) used in the above Process A, i.e. the formation of quaternary ammonium compound, may for example be trimethylamine, triethylamine, pyridine, thiazole, oxazole, N-methylmorpholine or N-methylpiperazine. This reaction is conducted using an equivalent to large excess (e.g. 50 equiv.) of base (III) per mole of compound (II) at room temperature or under heating (e.g. 35°–200° C.) either in the presence or absence of a solvent. The solvent may for example be methanol, toluene, benzene, ether, dioxane or tetrahydrofuran.

The compound (II) can be prepared, for example, as follows:

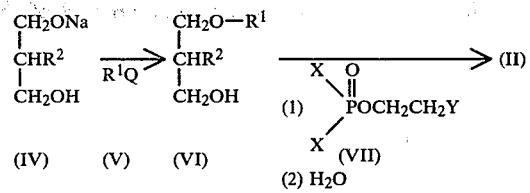

wherein Q is halogen, sulfate or sulfonate, X and Y are halogen (e.g. Cl, Br, I) and other symbols are as defined above.

In the starting compound (IV), sodium salt of 2-O-methylglycerol can be prepared by the methods described in Journal of The Chemical Society, 1934, p. 1234 or Annalen der Chemie, 709, p. 2421 (1967). Sodium salt of 1,3-propane diol can also be prepared by an analogous method thereto. This salt is dissolved or suspended in an inert solvent under anhydrous conditions and allowed to react with Compound (V).

Process B

Compound (I) wherein $R^4$ and $R^5$ are hydrogen and other symbols are as defined above, can also be produced by reacting a compound of the formula (VI) with a compound of the formula:

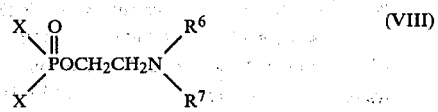

(VIII)

wherein X is as defined above, one of $R^6$ and $R^7$ corresponds to $R^3$ as defined above and another of $R^6$ and $R^7$ is protective group for amino, or

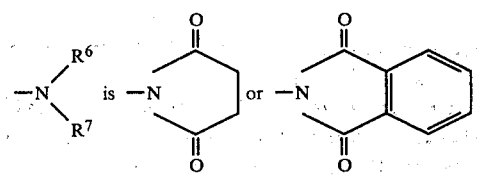

hydrolyzing the resulting compound, and then subjecting the hydrolyzed compound to a reaction for removal of the protective group.

The reaction of (VI) with (VIII) may be carried out in an inert solvent (e.g. benzene, chloroform) at a temperature within −20° C. to +50° C., and it may proceed advantageously in the presence of an appropriate bese (e.g. pyridine). The resulting compound is hydrolyzed in water or a mixture of water and an organic solvent (e.g. pyridine) at a room temperature or under heating. The hydrolyzed compound is subjected to a per se conventional reaction for removal of the protective group. For example, in the case that the amino group is protected in the form of phthalimide, hydrazinolysis is employed as a removal reaction of the protective group. Said reaction may be carried out in an inert solvent (e.g. methanol) under heating by using hydrozine hydrate.

The antitumor activity of analogous compounds, i.e. alkyl phospholipid representable by the afore-mentioned formula (I) wherein $R^1$ stands for octadecyl, hexadecyl dodecyl or decyl, has already been known from the abovementioned literature references. In these references, there is described an antitumor activity of alkyl phospholipid having an alkyl group (corresponding to $R^1$ in the formula (I)) of $C_{18}$, $C_{16}$, $C_{12}$ or $C_{10}$ at 3-position thereof. More concretely to state, it is disclosed that an alkyl lipid having a long chain of 16–18C is preferred (Japanese Patent Application Unexamined Publication No. 52-134027, p. 192 which corresponds to South African Pat. No. 772649), that 3-dodecyl compounds, as compared with 3-octadecyl compounds, show lower affinity to leukemia, and inhibitory action to multiplication of culture cells (leukemia in man) is lowered to about 1/10 of its original potency (Cancer Res. 38, p. 3896), and that, as the length of alkyl group chain is shortened from that of 3-hexadecyl compounds having a high activity, the antitumor activity is lowered, and 3-decyl compounds are entirely inactive (Cancer res. 38, p. 343 (lines 23–20 from the bottom). However, as to the alkyl phospholipid having such a chain-length of $C_{13}$ or $C_{14}$ as $R^1$ of the compound (I), no concrete description is found in the said reference.

The present inventors have succeeded in synthesizing these compounds, and found that they have especially excellent antitumor activity and, besides, excellent antifungal and antiprotozoal activities which have not been known in the compounds of this line.

The following are described in detail the characteristic pharmacological actions of the Compound (I).

The alkyl phospholipid having octadecyl is possessed of a very strong activity of controlling multiplication of tumor cells, and it has been known that the octadecyl compound is capable of controlling the multiplication of Methylchloanthrene induced tumor cell. BALB/c mice at a concentration of 1 μg/ml (Cancer Res. 39, pp. 4681–4686 (1979)). The present inventors conducted comparative tests between octadecyl phospholipid and the corresponding tridecyl compound as well as tetradecyl compound on the activity ($GD_{50}$) to inhibit the multiplication of spontaneous myeloid leukemia cells M1 in mice. The result was, as shown by Table 1 below, that in case of for example the tetradecyl compound, the value of $GD_{50}$ was 1.2 μg/ml against M1 cells, whereas that of the octadecyl compound was 0.6 μg/ml. The effect on the corresponding normal cells, i.e. on the myeloid cells of normal mice, is far weaker in the tetradecyl compounds. Therefore, in view of the balance of the inhibiting activity against multiplication of tumor cells and the safety (Chemotherapy Coefficient), it can be said that tetradecyl phospholipid is preferable to octadecyl phospholipid.

Generally stating, between tumor cells and normal cells of the corresponding tissue, differences are observed in various respects. What the phenotype, a characteristic feature of tumor cells, is like has been generally known, and it is also known as susceptible to change by the action of differentiation-inducing factor in vivo or by the treatment with a certain type of chemical substance. For example, there is sometimes observed disappearance of autonomic proliferativity or tumorigenetic activity (transplantation), these being characteristics of tumor cells. In these cases, the tumor cells show morphological changes from those in undifferentiated or slightly-differentiated state to normal cells or normal-like cells. For example, in spontaneous myeloid leukemia M1 cells in mice, it has been observed that they show phagocytic activity and wandering tendency in the process of differentiation and that ultimately they change into macrophages or granulocytes. At the same time, biochemical changes such as lysozyme activity or formation of reductase. Therefore, morphological changes, acquirement of phagocytic activity, and formation of lysozyme or reductase (NBT-reduction) are useful as typical functional markers of differentiation of tumor cells.

The following Tables 2 and 3 show the comparison of octadecyl phospholipids and tetradecyl phospholipids in their actions by the use of these markers. From these tables, it can be asserted that tetradecyl phospholipids are preferable compounds to octadecyl phospholipids from the viewpoint of the differentiation activity of tumor cells. Such tendency as above is observed also as to leukemia cells $R_{453}$ in mice induced by Raucher virus, human leukemia cells HL-60 or other various human tumors. Tridecyl phospholipids shows substantially similar strong activity to that of tetradecyl phospholipids. These alkyl-phospholipids is possessed of affinity to cell-membrane, and is supposed to act on cell-membrane of tumor cells. And, it is considered that, as the result of causing changes in the properties of cell-membrane, these alkyl-phospholipids show sometimes cell-cidal action and sometimes differentiation-inducing effect, thus inhibiting autonomic proliferativity of tumor cells. It is also considered that the action of these compounds to stimulate cell membrane naturally stimulates reticuloendothelial system resulting in displaying host-parasite antitumor effect. The Compound (I), namely in case where $R^1$ stands for tridecyl or tetradecyl, as compared with known octadecyl or hexadecyl compounds, is possessed of such characteristic features as lowering of hemolytic activity and giving less damage to tissues such as walls of blood vessel and muscles.

The compound can be administered as an antitumor agent with comparatively low toxicity to a warm-blooded animal, especially a mammal, afflicted by malignant tumors such as leukemia or solid tumor, and can produce significant life-span prolonging effect. Generally, the compound (I) is obtained in the form of a crystalline powder or a powder, and is sufficiently hydrophilic as well as lipophilic. When the compound is used as an antitumor agent, it can safely be administered parenterally or orally as it is or as a variety of pharmaceutical compositions such as injectable solution, tablet, capsule, solution or ointment.

Said pharmaceutical compositions may be prepared by admixing the compound (I) with a pharmaceutically acceptable carrier. More concretely, injectable solutions, solutions for drip infusion and the like containing the compound (I) can be prepared in a conventional manner using, for example, physiological saline or an aqueous solution containing glucose and/or other auxiliaries. Tablets, capsules and the like can also be prepared in a conventional manner. These are prepared as unit dosage forms and applied by an adequate route of administration depending on the purpose of administration thereof. In the case of injectable solutions, for instance, they are administered by intravenous or subcutaneous injection or directly applied to the affected resion. The dose for tumor-bearing warm-blooded animals can adequately be determined depending on the symptom, route of administration, etc., generally within the range of about 0.05–75 mg/kg body weight, preferably within the range of about 0.5–30 mg/kg body weight. As to the frequency of dosing, the drug can be administered daily or at 2- to 5-day intervals. It is also possible to administer the drug 1-4 times a day or by intravenous drip infusion so as to maintain the drug concentration in tissues at a required level for a prolonged period of time.

Furthermore, while the compound (I) has weak antibacterial activity, it has strong antimycotic and antiprotozoal activities. Thus, the Compound (I) is useful also as an antimycotic or antiprotozoan agent. Such antimycotic activity includes, among others, the activity against Trichophyton, Cryptococcus Unigtullatas and yeasts. Therefore, the compound (I) is useful in the treatment and prevention of diseases caused by these fungi, such as trichophytia.

The length of alkyl chain of the alkyl phospholipid exerts an influence upon its antimycotic activity also, as shown in Tables 5 and 6. From these tables, it is clear that the antimycotic activity of the alkyl phospholipids whose carbon number 13 or 14 is higher than those whose carbon number is less than 13 or more than 14, thus being preferable as an antimycotic agent.

Antimycotic preparations containing the compound (I) can be produced in a conventional manner. The amount of the active ingredient is not critical, but, when the preparations are used in the treatment of trichophytia, for instance, the amount of the compound of this invention is generally about 0.01–70% by weight, preferably about 0.1–5% by weight, based on the whole preparation. The anti-mycotic preparations can be administered in a conventional manner. Thus, for example, they are advantageously applied to or sprayed on the affected part once to several times a day.

The compound (I) of this invention is also active against phytopathogenic pests, especially fungi, hence is also useful as an agricultural fungicide for combating such plant diseases as rice blast, rice Helminthosporium leaf spot, rice stem rot, gray mold and cucumber anthracnose. Agricultural fungicide preparations containing the compound are made in a conventional manner. Adequate contents of the active ingredient are generally about 10–90% for emulsifiable concentrates, wettable powders and the like, about 0.1–10% for solutions, dusts and the like, and about 5–50% for granular preparations. Emulsifiable concentrates, wettable powders and the like should preferably be sprayed after adequate dilution with water or the like (e.g. 50–5,000-fold dilution). The agricultural fungicide preparations are applied by various methods known per se in such a manner that the active ingredient be applied generally in an amount of about 10–300 g per 10 ares and the concentration of the active ingredient desirably be in the range of about 10–1,000 ppm.

As to the activity of the compound (I) against protozoa, that of, for example, Tetrahymena is shown in Table 4. From the Table 4, it can be asserted that the compound (I) shows in this respect as well, substantially the same tendency as in the cases of its antitumor and antimycotic activities, namely, the antiprotozoal activity of alkylphospholipids whose carbon number is 13 or 14 is higher than those whose carbon number is less than 13 or higher than 14. Therefore the activity in association with the aforesaid antimycotic activity thereof makes the compound (I) of value as an antimycotic/antiprotozoal agent for the assay of bacterial ecologies in the soil, activated sludge, body fluids, etc. Thus, for example, in isolating useful bacteria from the soil, or in detecting the activity of bacteria alone to the exclusion of protozoa and fungi for operation or analysis of the activated sludge process in waste water treatment, selective growth of bacteria is possible without allowing fungi and protozoa present in the sample to grow. More detailedly, the test sample is added to a liquid or solid culture medium, then 0.1 ml of an aqueous solution of the compound (I) having a concentration of about 10 $\mu$g/ml to 100 mg/ml is added, and incubation is performed.

The following test examples, composition examples and preparation examples illustrate the present invention in more detail. However, they are by no means limitative of the present invention. Incidentally, in the chemical formulas for the compounds in the test examples, Me stands for methyl group (—CH$_3$).

TEST EXAMPLE 1

By employing Eagle's minimum essential medium supplemented with 10% heat-inactivated calf serum, incubation of spontaneous myeloid leukemia M1 cells (Resistant clone) harvested from mice (SL-strain) and normal bone marrow cells of mice of the same strain was conducted, in the presence or absence of the test compound in various concentrations, in a humified CO$_2$ incubator at 37° C. for 3 days. The number of viable cells was determined by the Trypan Blue Stain dye-exclusion test. The concentration of the tested compound for 50% inhibiting the proliferation of M1 cells or normal bone marrow cells (GD$_{50}$) was determined, and the result was shown in Table 1.

TABLE 1

Growth inhibitory activity to cultured mouse myeloid leukemia cells and normal bone marrow cells

| Compound | GD$_{50}$ ($\mu$g/ml) M1 cells (A) | Normal mouse bone marrow cells (B) | B/A |
|---|---|---|---|
| CH$_2$OC$_{18}$H$_{37}$<br>\|<br>CHOMe  (Control<br>\|   O      Compound)<br>\|   \|\|      +<br>CH$_2$OPOCH$_2$CH$_2$NMe$_3$<br>\|<br>O$^-$ | 0.6 | 15 | 25 |
| CH$_2$OC$_{14}$H$_{29}$<br>\|<br>CHOMe  (Present<br>\|   O      Compound)<br>\|   \|\|      +<br>CH$_2$OPOCH$_2$CH$_2$NMe$_3$<br>\|<br>OH | 1.2 | 40 | 33 |

TEST EXAMPLE 2

By employing soft-agar medium having similar components to those in Test Exampe 1, incubation of myeloid leukemia (M1) cells harvested from mice was conducted in the presence of the test compound in its optimal concentration. Observation on various biological and biochemical properties caused by induced differentiation was conducted. In Table 2 are given the results obtained by determination of the degree of the induced differentiation employing, as the indexes, among those properties, morphological changes (matured granulocytes, matured macrophages, others caused by changes in appearance of cells at the stage of differentiation), phagocytic activity (plastic small pieces.phagocytosis) and lysozyme activity. Additionally stating, these morphological changes were not observed under the conditions devoid of the drugs.

TABLE 2

Effects of alkyl-phospholipids on differentiation of mouse myeloid leukemia M1 cells

| Compound | Optimal dose (μg/ml) | Morphological change (%) | Phagocytic cells (%) | Lysozyme activity (units/mg protein) |
|---|---|---|---|---|
| None | | 2.1 | 2.0 | 2.2 |
| $CH_2OC_{18}H_{37}$<br>$\|$<br>$CHOMe$<br>$\phantom{x}\|\phantom{xx}O$<br>$\phantom{x}\|\phantom{xx}\|\phantom{xxx}+$<br>$CH_2OPOCH_2CH_2NMe_3$<br>$\phantom{xxxx}\|$<br>$\phantom{xxxx}O^-$ | 1 | 34.7 | 13.4 | 31.1 |
| $CH_2OC_{14}H_{29}$<br>$\|$<br>$CHOMe$<br>$\phantom{x}\|\phantom{xx}O$<br>$\phantom{x}\|\phantom{xx}\|\phantom{xxx}+$<br>$CH_2OPOCH_2CH_2NMe_3$<br>$\phantom{xxxx}\|$<br>$\phantom{xxxx}O^-$ | 2 | 53.4 | 25.9 | 80.1 |

TEST EXAMPLE 3

By employing soft-agar medium, incubation of human promyelocytic leukemia HL-60 cells was conducted in the presence of a drug at its optimal concentration. It was observed that the leukemia HL-60 cells were gradually changing into mature myeloid cells or phagocytic cells as the induced differentiation proceeded. After six day incubation, number of these cells was counted, and the respective ratios (%) relative to the total number of these cells were calculated, as shown in Table 3. Additionally stating, these changes were not observed under the conditions devoid of the drugs.

TABLE 3

Effects of alkyl-phospholipids on differentiation of human promyelocytic leukemia HL-60 cells

| Compound | Optimal dose (μg/ml) | Mature myeloid cells (%) | Phagocytic cells (%) | NBT* reduction (%) |
|---|---|---|---|---|
| $CH_2OC_{18}H_{37}$<br>$\|$<br>$CHOMe$<br>$\phantom{x}\|\phantom{xx}O$<br>$\phantom{x}\|\phantom{xx}\|\phantom{xxx}+$<br>$CH_2OPOCH_2CH_2NMe_3$<br>$\phantom{xxxx}\|$<br>$\phantom{xxxx}O^-$ | 1 | 43.0 | 39.8 | 47.8 |
| $CH_2OC_{14}H_{29}$<br>$\|$<br>$CHOMe$<br>$\phantom{x}\|\phantom{xx}O$<br>$\phantom{x}\|\phantom{xx}\|\phantom{xxx}+$<br>$CH_2OPOCH_2CH_2NMe_3$<br>$\phantom{xxxx}\|$<br>$\phantom{xxxx}O^-$ | 4 | 91.3 | 68.2 | 87.0 |

*nitro blue tetrazolium

TEST EXAMPLE 4

The antiprotozoal and antimycotic (antifungal) activities of some compounds in accordance with this invention are as shown in Tables 4 to 7.

Referring to the antiprotozoal activity given in Table 4, the microbial growth inhibiting activity (MIC) of each compound of this invention was assayed by the broth dilution method by incubating *Tetrahymena pyriformis* W strain as the test organism at 28° C. for 44–48 hours, using a test culture medium comprising 20 g of Tryptose peptine (Difco), 1 g of yeast extract, 2 g of glucose. 1,000 ml of distilled water and 10 ml of 1 M phosphate buffer (pH 7.0).

Referring to the antimycotic activity presented in Table 5, *Cryptococcus unigtullatas* and others were used as the test microbes, a paper disk (8 mm in diameter) was immersed in an aqueous solution of each test compound having a concentration of 3 mg/ml, air dried and placed on an agar medium, then incubation was conducted at 37° C. for 2 days, and the diameter (mm) of the inhibition zone was measured.

Referring to the antifungal activity shown in Table 6, a variety of typical phytopathogenic fungi were used as the test organisms, and the minimum inhibitory concentration (MIC) values were determined by the serial dilution method using 1% glucose-bouillon agar medium.

Referring to the antitrichophyton activity shown in Table 7, MIC values of tested compounds were determined by the serial dilution method using Sabouraud's agar medium.

TABLE 4

| MIC against *Tetrahymena pyriformis* W (μg/ml) | | | | |
|---|---|---|---|---|
| R— | $C_{18}H_{37}$— | $C_{14}H_{29}$— | $C_{13}H_{27}$— | $C_{12}H_{25}$— |
| $CH_2OR$<br>$\|$<br>$CHOMe$<br>$\phantom{x}\|\phantom{xx}O$<br>$\phantom{x}\|\phantom{xx}\|\phantom{xxx}+$<br>$CH_2OPOCH_2CH_2NMe_3$<br>$\phantom{xxxx}\|$<br>$\phantom{xxxx}O^-$ | 1 | 0.2 | 0.2–0.4 | 0.4 |

TABLE 4-continued

| MIC against Tetrahymena pyriformis W (μg/ml) | | | | |
|---|---|---|---|---|
| R— | $C_{18}H_{37}-$ | $C_{14}H_{29}-$ | $C_{13}H_{27}-$ | $C_{12}H_{25}-$ |
| $\begin{array}{l}CH_2OR\\|\\CHOMe\\|\quad O\\|\quad \|\\CH_2OPOCH_2CH_2NH_2\\|\\OH\end{array}$ | 4 | 2 | — | — |
| $\begin{array}{l}CH_2OR\\|\\CH_2\quad O\\|\quad \|\quad +\\CH_2OPOCH_2CH_2NMe_3\\|\\O^-\end{array}$ | 2–4 | 0.2 | 0.2 | 1 |
| $\begin{array}{l}CH_2OR\\|\\CH_2\quad O\\|\quad \|\\CH_2OPOCH_2CH_2NH_2\\|\\OH\end{array}$ | 4 | 0.4 | 0.4 | 2 |

TABLE 5

| Antimicrobial Activity against Cryptococcus unigtullatas Inhibition zone diameters (mm) at the concentration of 3 mg/ml | | | | |
|---|---|---|---|---|
| R— | $C_{18}H_{37}-$ | $C_{14}H_{29}-$ | $C_{13}H_{27}-$ | $C_{12}H_{25}-$ |
| $\begin{array}{l}CH_2OR\\|\\CHOMe\\|\quad O\\|\quad \|\quad +\\CH_2OPOCH_2CH_2NMe_3\\|\\O^-\end{array}$ | 18 | 22 | 19 | 15 |
| $\begin{array}{l}CH_2OR\\|\\CHOMe\\|\quad O\\|\quad \|\\CH_2OPOCH_2CH_2NH_2\\|\\OH\end{array}$ | <5 | 13.5 | — | <5 |
| $\begin{array}{l}CH_2OR\\|\\CH_2\quad O\\|\quad \|\quad +\\CH_2OPOCH_2CH_2NMe_3\\|\\O^-\end{array}$ | 17 | 21 | 20 | 19 |

TABLE 6

Antifungal Activity (MIC: μg/ml)

(A)
$$\begin{array}{l}CH_2O-R\\|\\CHOMe\\|\quad O\\|\quad \|\quad +\\CH_2OPOCH_2CH_2NMe_3\\|\\O^-\end{array}$$

(B)
$$\begin{array}{l}CH_2O-R\\|\\CH_2\quad O\\|\quad \|\quad +\\CH_2OPOCH_2CH_2NMe_3\\|\\O^-\end{array}$$

| Phytopathogenic fungus | R in Compound (A) | | | | R in Compound (B) | | | |
|---|---|---|---|---|---|---|---|---|
| | $C_{18}H_{37}$ | $C_{14}H_{29}$ | $C_{13}H_{27}$ | $C_{12}H_{25}$ | $C_{18}H_{37}$ | $C_{14}H_{29}$ | $C_{13}H_{27}$ | $C_{12}H_{25}$ |
| *Pyricularia oryzae* (rice blast) | 6.25 | 3.12 | 12.5 | 25 | 12.5 | 6.25 | 6.25 | 12.5 |
| *Cochliobolus miyabeanus* (rice Helminthosporium leaf spot) | >100 | 12.5 | >100 | >100 | >100 | 12.5 | 6.25 | 6.25 |
| *Gibberella fujikuroi* (rice Bakanae-disease) | >100 | 25 | >100 | >100 | >100 | 12.5 | 25 | 100 |

TABLE 6-continued

Antifungal Activity (MIC: μg/ml)

$$\begin{array}{c} CH_2O-R \\ | \\ CHOMe \\ | \quad O \\ | \quad \| \\ CH_2OPOCH_2CH_2\overset{+}{N}Me_3 \\ | \\ O^- \end{array} \qquad \begin{array}{c} CH_2O-R \\ | \\ CH_2 \quad O \\ | \quad \| \\ CH_2OPOCH_2CH_2\overset{+}{N}Me_3 \\ | \\ O^- \end{array}$$

(A)  (B)

| Phytopathogenic fungus | R in Compound (A) | | | | R in Compound (B) | | | |
|---|---|---|---|---|---|---|---|---|
| | $C_{18}H_{37}$ | $C_{14}H_{29}$ | $C_{13}H_{27}$ | $C_{12}H_{25}$ | $C_{18}H_{37}$ | $C_{14}H_{29}$ | $C_{13}H_{27}$ | $C_{12}H_{25}$ |
| *Botrytis cinerea* (gray mold) | 25 | 6.25 | 12.5 | 50 | 25 | 6.25 | 6.25 | 25 |
| *Alternaria solani* (potato early blight) | >100 | 100 | 50 | 50 | >100 | 50 | 25 | 50 |
| *Leptosphaeria salvinii* (rice stem rot) | 12.5 | 3.12 | 6.25 | 25 | 50 | 6.25 | 12.5 | 25 |
| *Colletotrichum lagenarium* (cucumber anthracnose) | >100 | 25 | 6.25 | 12.5 | >100 | 6.25 | 1.56 | 6.25 |

TABLE 7 antitrichophyton activity $$\begin{array}{c} CH_2O-R \\ | \\ CHOMe \\ | \quad O \\ | \quad \| \\ CH_2OPOCH_2CH_2A \\ | \\ O^- \end{array}$$

| Compound | | MIC (μg/ml) | |
|---|---|---|---|
| R | A | DT-66* | DT-63* |
| $C_{12}H_{25}$ | $-\overset{+}{N}Me_3$ | 25 | 6.25 |
| $C_{13}H_{27}$ | $-\overset{+}{N}Me_3$ | 6.25 | 3.12 |
| $C_{13}H_{27}$ | 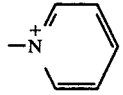 | 12.5 | 3.12 |
| $C_{14}H_{29}$ | $-\overset{+}{N}Me_3$ | 3.12 | 1.56 |
| $C_{14}H_{29}$ | 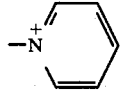 | 3.12 | 1.56 |

*Tested microorganism
DT-66: *Trichophyton mentagrophytes* IFO 5809
DT-63: *Trichophyton rubrum* IFO 5467

DOSAGE FORM EXAMPLE 1

3-Tridecyloxy-2-methoxypropyl 2-trimethylammonioethyl phosphate (80 g) is dissolved in 1 liter of distilled water, the solution is passed through a sterilization filter, poured into 1,000 vials (1 ml per vial) and lyophilized, and the vials are tightly stoppered.

Separately, a solution containing xylitol or mannitol (100 g in 2 liters) in distilled water for injection is poured into 1,000 ampules for injectable solution (2 ml per ampule) in an aseptic manner, and the ampules are sealed by fusing.

For administration, the powder in one vial is dissolved in the above-mentioned xylitol (or mannitol) solution in one ampule.

DOSAGE FORM EXAMPLE 2

Tablets, each weighting 370 mg and having a diameter of 9.5 mm, are prepared in a conventional manner by mixing the ingredients:

| | | |
|---|---|---|
| (1) | 3-Tridecyloxo-2-methoxypropyl 2-trimethylammonioethyl phosphate | 100 mg per tablet |
| (2) | Lactose | 200 mg per tablet |
| (3) | Corn starch | 51 mg per tablet |
| (4) | Hydroxypropylcellulose | 9 mg per tablet |

DOSAGE FORM EXAMPLE 3

The tablets in Dosage Form Example 2 are coated with a solution of hydroxypropylmethylcellulose phthalate (14 mg per tablet) and castor oil (1 mg per tablet) in an acetone-ethanol (4:6) mixture, the concentration of the solutes being 7%. Thus are obtained enteric coated tablets.

EXAMPLE 1

3-Tetradecyloxypropanol

In 70 ml of a mixture of dimethylsulfoxide-tetrahydrofuran (1:1) are dissolved 12.3 g of trimethylene glycol and 15 g of tetradecyl bromide. To the solution is added 12 g of powdery potassium hydroxide. The mixture is vigorously stirred for one hour at a room temperature, which is refluxed under heating for two hours. The reaction mixture is poured into 400 ml of cold water, which is neutralized and subjected to extraction with ethyl acetate, then washed with water and dried. The resultant is concentrated to dryness, and the residue is dissolved in methanol when hot. Cooling of the solution gives precipitation of crystals, which are removed by filtration. The filtrate is refined by means of chromatography employing silica-gel (eluent: chloroform) to give 5.1 g of the end-product.

EXAMPLE 2

3-Tetradecyloxypropyl 2-trimethylammonioethyl phosphate

In 30 ml of benzene are dissolved 4.64 g of the alcohol obtained in Example 1 and 6.19 g of 2-bromoethylphosphorous dichloride. While the solution is cooled with ice, 2.02 g of pyridine is added thereto dropwise, and the mixture is stirred at a room temperature for one hour. The mixture is subjected to distillation to remove benzene, then 50 ml of water is added thereto, followed by refluxing for 1.5 hours. The reaction mixture, after cooling, is subjected to extraction with ether, and the extract is concentrated to dryness. The concentrate is dissolved in 40 ml of toluene containing 8 g of triethylamine, which is heated at 60° C. for two days. Methanol is then employed as the solvent, 3.53 g of silver carbonate is added to the reaction mixture, followed by refluxing for 1.5 hours. The resultant is subjected to filtration when hot, and the filtrate is concentrated to dryness to give a crude product, this is refined by means of chromatography using silica-gel, followed by recrystallization from a mixture of chloroform-acetone to afford 3.5 g (47%) of the end-product.

Elemental analysis: $C_{22}H_{48}NO_5P \cdot H_2O$; Theoretical value: C, 58.00; H, 11.06; N, 3.07; P, 6.80; Experimental value: C, 57.82; H, 11.22, N, 2.98; P, 6.87.

EXAMPLE 3

2-Methoxy-3-tridecyloxypropanol

In a mixture of 40 ml of dimethylsulfoxide and 40 ml of tetrahydrofuran are dissolved 12.11 g (46 mmol) of 1-bromotridecane and 14.63 g (138 mmol) of β-O-methylglycerin. To the solution is added 10.324 g (184 mmol) of powdery potassium hydroxide, and the mixture is stirred at a room temperature for two hours. In accordance with conventional procedure, the reaction solution is poured into water, subjected to neutralization, subjected to extraction with ethyl acetate, followed by refining by means of silica-gel chromatography to afford 11.5 g of the desired alcohol compound.

NMR ($D_6$-DMSO, 60MC) 0.92(3H), 1.13, 1.73(22H), 1.83(2H), 3.33(10H), 4.67(1H).

EXAMPLE 4

3-Tridecyloxy-2-methoxypropyl 2-trimethylammonioethyl phosphate

In 47 ml of benzene are dissolved 8.0 g (27.73 mmol) of the alcohol compound obtained in Example 3 and 10.0 g (41.6 mmol) of 2-bromoethylphosphorous dichloride. To the solution is added 3.29 g (41.6 mmol) of pyridine gradually, and the mixture is stirred vigorously at a room temperature for two hours. The reaction solution is subjected, after the manner in Example 2, to hydrolysis, quaternarization and dehalogenation, which is then subjected to refining by means of silica-gel chromatography to afford 5.0 g of the end-product as colorless solid substance.

IR (film)cm$^{-1}$: 3350, 2920, 2850, 1650, 1460, 1080, 1050, 960, 760.

Elemental analysis: $C_{22}H_{48}O_6P$; Theoretical value: C, 57.34; H, 10.67; N, 3.04; P, 6.72; Experimental value: C, 57.46; H, 10.71; N, 3.11; P, 6.70.

EXAMPLE 5

3-Tridecyloxypropanol

After the manner described in Example 3, 12.11 g (46 mmol) of 1-bromotridecane and 10.2 g (138 mmol) of propanediol are processed to afford 10.0 g of the desired alcohol compound.

EXAMPLE 6

3-Tridecyloxypropyl 2-trimethylammonioethyl phosphate

In 25 ml of benzene are dissolved 4.0 g (15.48 mmol) of 3-tridecyloxypropanol obtained in Example 5 and 5.62 g (23.22 mmol) of 2-bromoethylphosphorous dichloride. To the solution is added dropwise 1.83 g (23.22 mmol) of pyridine, and the mixture is stirred at a room temperature for two hours. The reaction solution is subjected, after the manner described in Example 2, to hydrolysis, quaternarization and dehalogenation, followed by refining by means of silica-gel chromatography to afford 2.5 g of the endproduct as colorless powder.

IR (film)cm$^{-1}$: 3390, 2920, 2850, 1650, 1230, 1085, 1055, 960, 750.

Elemental analysis: $C_{21}H_{46}NO_5P \cdot H_2O$; Theoretical value: C, 57.12; H, 10.96; N, 3.17; P, 7.01; Experimental value: C, 56.86; H, 10.86; N, 3.09; P, 7.33.

EXAMPLE 7

3-Tridecycloxypropyl 2-aminoethyl phosphate

In 12 ml of benzene are dissolved 2.0 g (7.74 mmol) of the alcohol compound obtained in Example 5 and 3.1 g (10.06 mmol) of 2-phthalimidophosphorous dichloride. To the solution is added 0.79 g (10.06 mmol) of pyridine, and the mixture is stirred for two hours. The reaction solution is subjected to hydrolysis with 70% pyridine, processed with hydrazine hydrate, then refined by means of silicagel chromatography, followed by recrystallization from 50 ml of methanol to afford 1.8 g of colorless crystals.

IR (film)cm$^{-1}$: 2910, 2850, 1650, 1460, 1370, 1240, 1220, 1110, 1080, 1010, 1000, 915, 770.

Elemental analysis: $C_{18}H_{40}NO_5P$; Theoretical value: C, 56.67; H, 10.57; N, 3.67; P, 8.12; Experimental value: C, 57.01; H, 10.55; N, 4.02; P, 8.31.

EXAMPLE 8

2-Methoxy-3-tetradecyloxypropanol

In a mixture of 25 ml of dimethylsulfoxide and 25 ml of tetrahydrofuran are dissolved 8.75 g ($3.16 \times 10^{-2}$ mol) of 1-bromotetradecane and 10 g ($9.42 \times 10^{-2}$ mol) of β-O-methyl glycerin. To the solution is added 7 g ($1.25 \times 10^{-1}$ mol) of powdery KOH, and the mixture is stirred at a room temperature for two hours. The reaction solution is poured into water in accordance with conventional manner, neutralized, subjected to extraction with ethyl acetate, then refined by means of silica-gel chromatography, whereby 4.2 g of the desired alcohol compound is obtained.

IR (liq)cm$^{-1}$: 3425, 2925, 2850, 1460, 1115, 751

EXAMPLE 9

(3-Tetradecyloxy-2-methoxy)propyl 2-trimethylammonioethyl phosphate

In 50 ml of benzene are dissolved 5 g ($1.65 \times 10^{-2}$ mol) of the alcohol compound obtained in Example 8 and 5.19 g ($2.15 \times 10^{-2}$ mol) of 2-bromoethylphosphorous dichloride. To the solution is added dropwise 2.61 g ($3.3 \times 10^{-2}$ mol) of pyridine, and the mixture is vigorously stirred at a room temperature for two hours. The reaction solution is subjected, in accordance with the manner described in Example 2, to hydrolysis, quaternarization and dehalogenation, followed by refining by means of silica-gel chromatography to afford 1.0 g of the end-product as white powder.

IR (KBr)cm$^{-1}$: 3400, 2900, 2840, 1460, 1222, 1080
Elemental analysis: $C_{23}H_{50}NO_6P\cdot1/2H_2O$; Theoretical value: C, 57.95; H, 10.79; N, 2.94; P, 6.49; Experimental value: C, 57.55; H, 10.74; N, 3.05, P, 6.40.

EXAMPLE 10

(3-Tetradecyloxy-2-methoxy)propyl 2-aminoethyl phosphate

In 23 ml of benzene are dissolved 3.0 g ($9.92\times10^{-3}$ mol) of the alcohol compound obtained in Example 8 and 3.97 g ($1.29\times10^{-2}$ mol) of 2-phthalimidophosphorous dichloride. To the solution is added dropwise 1.2 g ($1.49\times10^{-2}$ mol) of pyridine, and the mixture is stirred vigorously at a room temperature for three hours. The reaction solution is subjected to hydrolysis with 70% pyridine, processed with hydrazine hydrate, refined by means of silica-gel chromatography, followed by recrystallization from 60 ml of methanol to afford 2.31 g of white powder.

IR(KBr)cm$^{-1}$: 2920, 2845, 1560, 1460, 1218, 1070, 910

Elemental analysis: $C_{20}H_{44}NO_6P$ mp. 195°–200° C. Theoretical value: C, 56.45; H, 10.42; N, 3.29; P, 7.28; Experimental value: C, 56.62; H, 10.11; N, 3.50; P, 7.31.

EXAMPLE 11

3-Tridecyloxy-2-methoxypropyl 2-pyridinioethyl phosphate

In 20 ml of benzene are dissolved 2.0 g ($6.93\times10^{-3}$ mol) of the alcohol compound obtained in Example 3 and 2.5 g ($1.04\times10^{-2}$ mol) of 2-bromoethylphosphorous dichloride. To the solution is added dropwise 0.82 g ($1.04\times10^{-2}$ mol) of pyridine. The mixture is stirred vigorously at a room temperature for two hours. Benzene is removed by distillation, and to the residue is added 40 ml of water. The mixture is subjected to reflux under heating. After cooling, 4 ml of concentrated hydrochloric acid is added, which is subjected to extraction with ether, followed by concentration to dryness. The residue is dissolved in 12 ml of pyridine, then the solution is stirred at a room temperature overnight. After completion of the reaction methanol is employed as the solvent, to which is added 2.5 g ($9\times10^{-3}$ mol) of silver carbonate. The mixture is refluxed for 1.5 hours under heating, then subjected to filtration when hot, and the filtrate is concentrated to dryness to give crude product, which is refined by means of silica-gel chromatography, followed by recrystallization from a mixture of chloroform and acetone to afford 0.6 g (18%) of the end-product.

IR (KBr)cm$^{-1}$: 3420, 2922, 2850, 1630, 1490, 1240, 1070.

Elemental analysis: $C_{24}H_{44}NO_6P\cdot H_2O$. Theoretical value: C, 58.64; H, 9.43; N, 2.85; P, 63.0; Experimental value: C, 58.27; H, 9.44; N, 3.09; P, 5.94.

EXAMPLE 12

(3-Tetradecyloxy-2-methoxy)propyl 2-pyridinioethyl phosphate

A similar reaction to that of Example 11 is applied to 2.46 g of 3-tetradecyl-2-methoxypropanol obtained in Example 8 to give 0.61 g of the title compound.

IR (KBr)cm$^{-1}$: 2920, 2850, 1230, 1070

Elemental analysis: $C_{25}H_{46}NO_6P\cdot H_2O$; Theoretical value: C, 59.39; H, 9.57; N, 2.77; P, 6.13; Experimental value: C, 59.09; H, 9.14; N, 2.71; P, 6.07.

EXAMPLE 13

(2R)-(3-Tetradecyloxy-2-methoxy)propyl 2-pyridinioethyl phosphate (1) A similar reaction of Example 8 is applied to 6.6 g of 1,2-isopropylidene-D-glycerol and 29 g of tetradecylbromide to give 12.6 g of 1,2-isopropylidene-3-tetradecyl-sn-glycerol.

IR (neat)cm$^{-1}$: 2920, 2850, 1460, 1110, 840

TLC: Rf=0.4 (one spot, n-hexane-ethyl acetate=10:1) $[\alpha]_D^{23}=+11.83°$ (in substance)

(2) In 20 ml of dioxane is dissolved 11.08 g of 1,2-isopropylidene-3-tetradecyl-sn-glycerol. After addition of 5 ml of 10% hydrochloric acid, the solution is stirred overnight at a room temperature. The reaction mixture is cooled with ice and the resulting precipitates are collected by filtration. The filtrate is refined by chromatography on silica gel (eluent: n-hexane-ethyl acetate=3:1) and combined to the collected product to give 7.8 g of 3-tetradecyl-sn-glycerol.

IR (KBr)cm$^{-1}$: 3420, 3340, 2920, 2850, 1460, 1130.
NMR(60 MHz, CDCl$_3$): 0.87(3H), 1.27(24H), 3.3–4.0(7H), $[\alpha]_D=-2.2°$ (c=1, CHCl$_3$)
m.p. 56.0°–56.5° C.

(3) In 30 ml of pyridine, 5.76 g of 3-tetradecyl-sn-glycerol is allowed to react with 8.39 g of p-toluenesulfonic acid chloride to give 9.6 g (81%) of 1,2-ditosyl-3-tetradecyl-sn-glycerol. This ditosyl compound (9.6 g) is dissolved in 80 ml of ethanol, followed by addition of 7.89 g of fused potassium acetate. After 40 hours of reflux, the reaction mixture is cooled and the resulting precipitates are removed by filtration. The solvent is distilled off and the residue is dissolved in a methanol solution (300 ml) containing 3 g of sodium methoxide. The solution is refluxed for 2 hours and the solvent is removed by distillation. To the residue are added chloroform and water for separation and the chloroform layer is washed with water, dried and subjected to chromatography on silica gel to give 2.82 g of 1-tetradecyl-sn-glycerol.

m.p. 56°–57° C.
$[\alpha]_D=+2.2°$ (c=1, CHCl$_3$)

(4) In 30 ml of dry pyridine, 2.82 g of 1-tetradecyl-sn-glycerol is allowed to react 3.27 g of triphenylchloromethane to give 1-tetradecyl-3-trityl-sn-glycerol. This compound is subjected to methylation with methyl iodide and deprotection to give 2 g of 1-tetradecyl-2-methyl-sn-glycerol.

IR (film)cm$^{-1}$: 3430, 2920, 2855, 1465, 1110, 735
NMR (60 MHz, CDCl$_3$): 0.87(3H,s), 1.27(24H,m), 2.90(1H), 3.46(3H,s), 3.3–3.8(5H,m)
$[\alpha]_D=-11.0°$ (c=1, CHCl$_3$)

(5) A similar reaction to that of Example 11 is applied to 500 mg of 1-tetradecyl-2-methyl-sn-glycerol to give 206 mg of the title compound, namely (2R)-(3-tetradecyloxy-2-methoxy)propyl 2-pyridinioethyl phosphate.

IR (KBr)cm$^{-1}$: 3400, 2920, 2850, 1630, 1230, 1070, 905, 730
NMR (60 MHz, CHCl$_3$); 0.87(3H,s), 1.27(24H,m), 3.37(9H,s), 3.3–4.5(9H,m), 5.1(2H,CH$_2$N), 8.2(2H), 8.5(1H), 9.33(2H)
$[\alpha]_D=+1.2°$ (c=1, CHCl$_3$)

EXAMPLE 14

(2S)-(3-Tetradecyloxy-2-methoxy)propyl 2-pyridinioethyl phosphate (1) A similar reaction to that of Example 13-(4) is applied to 2.30 g of 3-tetradecyl-sn-glycerol obtained in Example 13-(2) to give 1.0 g of 3-tetradecyl-2-methyl-sn-glycerol.

$[\alpha]_D = +10.0°$ (c=2, CHCl$_3$)

(2) A similar reaction to that of Example 13-(5) is applied to 600 mg of 3-tetradecyl-2-methyl-sn-glycerol to give 260 mg of the title compound.

$[\alpha]_D = -1.4°$ (c=1, CHCl$_3$)

TLC: Rf=0.20 (one spot, chloroform-methanol-water=65:25:4)

EXAMPLE 15

(2R)-(3-Tetradecyloxy-2-methoxy)propyl 2-trimethylammonioethyl phosphate

A similar reaction to that of Example 2 is applied to 1.5 g of 1-tetradecyl-2-methyl-sn-glycerol to give 1.2 g of the title compound.

IR (film)cm$^{-1}$: 3380, 2910, 2850, 1460, 1225, 1080, 1060

NMR (60 MHz, CDCl$_3$): 0.87(3H), 1.27(24H), 3.38(9H), 3.41(3H), 3.2–4.4(11H)

$[\alpha]_D = -2.4°$ (c=1, CHCl$_3$)

EXAMPLE 16

(2S)-(3-Tetradecyloxy-2-methoxy)propyl 2-trimethylammonioethyl phosphate

A similar reaction to that of Example 2 is applied to 200 mg of 3-tetradecyl-2-methyl-sn-glycerol obtained in Example 13-(2) to give 60 mg of the title compound.

$[\alpha]_D = +2.3°$ (c=1, CHCl$_3$)

TLC:Rf=0.16 (one spot, chloroform-methanol-water=65:25:4)

What is claimed is:

1. A compound of the formula

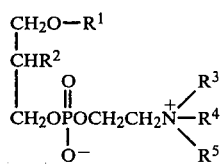

wherein
R$^1$ is tridecyl or tetradecyl,
R$^2$ is hydrogen or —OCH$_3$, and

is pyridinio, oxazolio or thiazolio
or a pharmaceutically acceptable salt thereof.

2. A compound of the formula

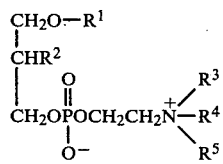

wherein
R$^1$ is tridecyl or tetradecyl,
R$^2$ is hydrogen or —OCH$_3$, and

is pyridinio
or a pharmaceutically acceptable salt thereof.

3. A compound of the formula

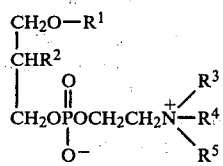

wherein
R$^1$ is tridecyl or tetradecyl
R$^2$ is hydrogen or —OCH$_3$, and

is oxazolio,
or a pharmaceutically acceptable salt thereof.

4. The compound which is (3-tetradecyloxy-2-methoxy)propyl 2-pyridinioethyl phosphate.

5. The compound which is (3-tridecyloxy-2-methoxy)propyl 2-pyridinioethyl phosphate.

* * * * *